US010695972B2

(12) United States Patent
Pleasants et al.

(10) Patent No.: US 10,695,972 B2
(45) Date of Patent: *Jun. 30, 2020

(54) TESTING APPARATUS USED FOR CURED SAMPLE LINERS USED IN REHABILITATION OF PIPELINE HAVING SAMPLE LINER EXPOSED TO PRESSURE AND UV LIGHT

(71) Applicant: RELINE AMERICA, INC., Clarksburg, MD (US)

(72) Inventors: David Samuel Pleasants, Monrovia, MD (US); William Donald Pleasants, Jr., Boyds, MD (US)

(73) Assignee: RELINE AMERICA, INC., Clarksburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/382,377

(22) Filed: Apr. 12, 2019

(65) Prior Publication Data

US 2019/0232549 A1    Aug. 1, 2019

Related U.S. Application Data

(63) Continuation of application No. 15/287,967, filed on Oct. 7, 2016, now Pat. No. 10,300,656.
(Continued)

(51) Int. Cl.
*G01N 33/44* (2006.01)
*G01N 25/48* (2006.01)
(Continued)

(52) U.S. Cl.
CPC ...... *B29C 63/0052* (2013.01); *B29C 35/0805* (2013.01); *G01N 3/12* (2013.01);
(Continued)

(58) Field of Classification Search
CPC ... B29C 51/10; B29C 51/14; B29C 2795/005; B29C 51/16; B29C 51/262;
(Continued)

(56) References Cited

U.S. PATENT DOCUMENTS 3,368,471 A * 2/1968 Beato ............... B29C 51/10
355/91
5,321,356 A * 6/1994 Weischedel ............ G01N 27/82
324/240
(Continued)

*Primary Examiner* — Brandi N Hopkins
(74) *Attorney, Agent, or Firm* — Welsh Flaxman & Gitler LLC

(57) ABSTRACT

A testing apparatus for onsite creation of cured sample liners necessary for confirming proper rehabilitation of pipelines includes a testing box having a base with a plurality of upstanding side walls defining an open upper end of the testing box. The testing box also includes an electrical power control assembly and an ultraviolet light assembly. A liner support manifold is shaped and dimensioned for supporting a sample liner and for attachment to the open upper end of the testing box for exposing the sample liner to pressure and ultraviolet light. In practice, and with the sample liner secured to the liner support manifold and the liner support manifold secured to the testing box, the sample liner is exposed to pressure and UV light in a highly controlled manner allowing for replication of actual in-line curing processing.

4 Claims, 10 Drawing Sheets

Related U.S. Application Data

(60) Provisional application No. 62/239,523, filed on Oct. 9, 2015.

(51) Int. Cl.
| | |
|---|---|
| *B29C 63/00* | (2006.01) |
| *G01N 3/12* | (2006.01) |
| *B29C 35/08* | (2006.01) |
| *G01N 7/00* | (2006.01) |
| *G01N 21/75* | (2006.01) |
| *F16L 55/18* | (2006.01) |

(52) U.S. Cl.
CPC ............... *G01N 7/00* (2013.01); *G01N 21/75* (2013.01); *G01N 25/4846* (2013.01); *G01N 33/442* (2013.01); *B29C 2035/0827* (2013.01); *F16L 55/18* (2013.01); *G01N 2203/0044* (2013.01); *G01N 2203/0092* (2013.01)

(58) Field of Classification Search
CPC ......... B29C 2791/007; B29C 2791/006; G03F 7/0037; B29L 2031/7602; Y10S 425/048
See application file for complete search history.

(56) References Cited

U.S. PATENT DOCUMENTS

| | | | |
|---|---|---|---|
| 6,250,909 B1 * | 6/2001 | Segen, Jr. ............. | B29C 51/262 425/400 |
| 9,090,114 B1 * | 7/2015 | Stumm ................ | B41M 7/0045 |

\* cited by examiner

TESTING APPARATUS USED FOR CURED SAMPLE LINERS USED IN REHABILITATION OF PIPELINE HAVING SAMPLE LINER EXPOSED TO PRESSURE AND UV LIGHT

CROSS REFERENCE TO RELATED APPLICATION

This application is a continuation of U.S. patent application Ser. No. 15/287,967, entitled "TESTING APPARATUS USED FOR CURED SAMPLE LINERS USED IN REHABILITATION OF PIPELINE HAVING SAMPLE LINER EXPOSED TO PRESSURE AND UV LIGHT" filed Oct. 7, 2016, which claims the benefit of U.S. Provisional Patent Application Ser. No. 62/239,523, entitled "TESTING APPARATUS FOR CURED LINERS USED IN PIPELINE REHABILITATION," filed Oct. 9, 2015.

BACKGROUND OF THE INVENTION

1. Field of the Invention

The present invention generally relates to a testing apparatus for cured liners used in pipeline rehabilitation.

2. Description of the Related Art

It is well appreciated that regulations require testing of pipeline liners to ensure the actual liner within the pipeline (the in-ground liner) meets the engineered design characteristics. Such cured liners are commonly resin impregnated fiberglass and require the application of ultraviolet (UV) light to ensure full and proper curing in place within the pipeline.

Presently, it is necessary to cut out a sample of a liner actually installed within the pipeline. The cutout sample is then tested to confirm that the in-ground liner meets the engineered design characteristics. This process is time consuming and unreliable.

SUMMARY OF THE INVENTION

It is, therefore, an object of the present invention to provide a testing apparatus for onsite creation of cured sample liners necessary for confirming proper rehabilitation of pipelines. The testing apparatus includes a testing box having a base with a plurality of upstanding side walls defining an open upper end of the testing box. The testing box also includes an electrical power control assembly and an ultraviolet light assembly. A liner support manifold is shaped and dimensioned for supporting a sample liner and for attachment to the open upper end of the testing box for exposing the sample liner to pressure and ultraviolet light. In practice, and with the sample liner secured to the liner support manifold and the liner support manifold secured to the testing box, the sample liner is exposed to pressure and UV light in a highly controlled manner allowing for replication of actual in-line curing processing.

It is also an object of the present invention to provide a testing apparatus wherein each of the side walls includes a lower end secured to an edge of the base and an upper edge, and wherein the upper edges of the side walls define the open upper end of the testing box.

It is another object of the present invention to provide a testing apparatus wherein the testing box includes a pressure input for attachment to a source of pressure and a pressure output (or sensor coupling port) for monitoring the pressure when the testing process is taking place.

It is a further object of the present invention to provide a testing apparatus wherein the testing box includes a temperature gauge coupled to one of the side walls for ready observation of the temperature within the testing box.

It is also an object of the present invention to provide a testing apparatus wherein the ultraviolet light assembly is positioned within a center of a cavity defined by the side walls of the testing box.

It is another object of the present invention to provide a testing apparatus wherein the ultraviolet light assembly is mounted within the testing box in a manner allowing for selective movement of the ultraviolet light assembly toward or away from the sample liner.

It is a further object of the present invention to provide a testing apparatus wherein the testing box includes vertically oriented first and second support posts upon which the ultraviolet light assembly is mounted for selective movement relative thereto.

It is also an object of the present invention to provide a testing apparatus wherein the liner support manifold includes a cover member and a frame coupling member between which the sample liner is mounted.

It is another object of the present invention to provide a testing apparatus wherein the electrical power control assembly includes a coupling member for attachment to a source of power.

It is a further object of the present invention to provide a testing apparatus wherein the frame coupling member includes a plurality of elongated members coupled together such that the frame coupling member includes an upper surface, a lower surface, an interior periphery, and an exterior surface.

It is also an object of the present invention to provide a testing apparatus wherein a bottom of the cover member includes a recess into which the sample liner forms as it is cured under ultraviolet light and pressure.

It is another object of the present invention to provide a testing apparatus wherein the cover member is provided with at least one relief hole to allow for the evacuation of pressure between the bottom of the cover member and the sample liner as the sample liner moves toward the bottom of the cover member.

It is a further object of the present invention to provide a testing apparatus wherein the liner support manifold includes a plurality of coupling members selectively securing the cover member and the frame coupling member with the sample liner is mounted therebetween.

It is also an object of the present invention to provide a testing apparatus wherein a rubber sealing member is positioned between the liner support manifold and the open upper end of the testing box.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
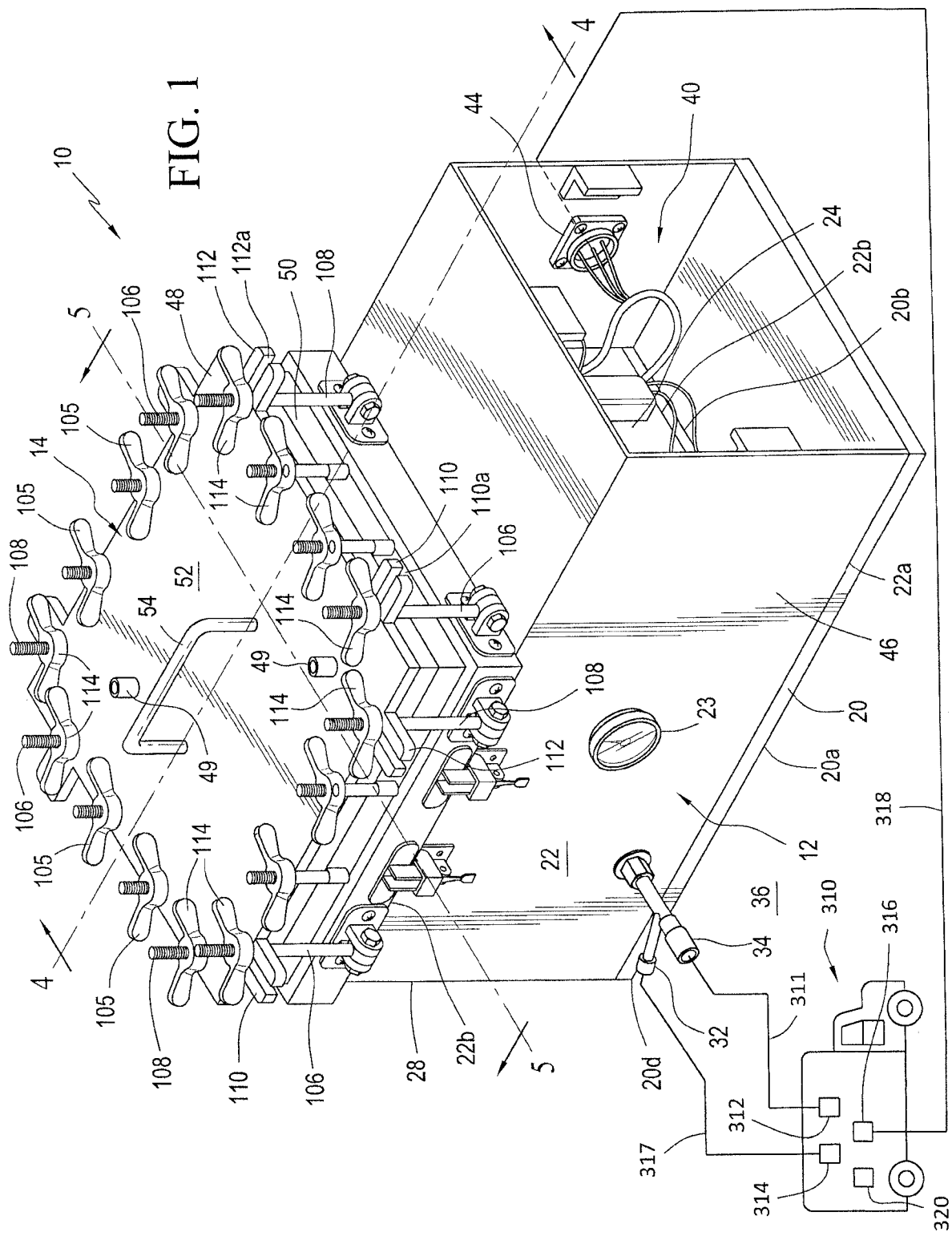
FIG. 1 is a perspective view of an embodiment of the testing apparatus in accordance with the present invention.
Figure 2:
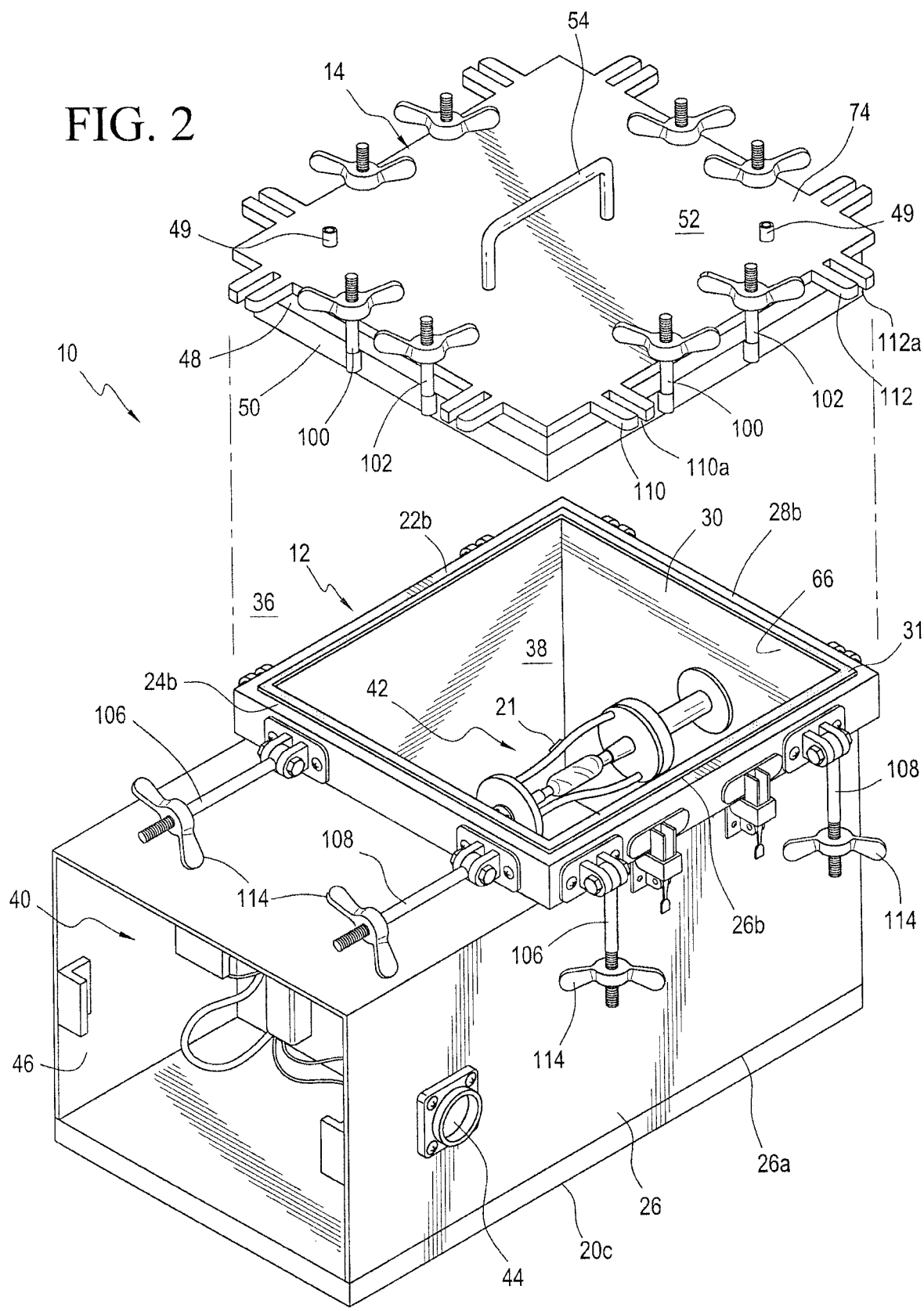
FIG. 2 is an exploded view of the testing apparatus shown in FIG. 1.
Figure 3:
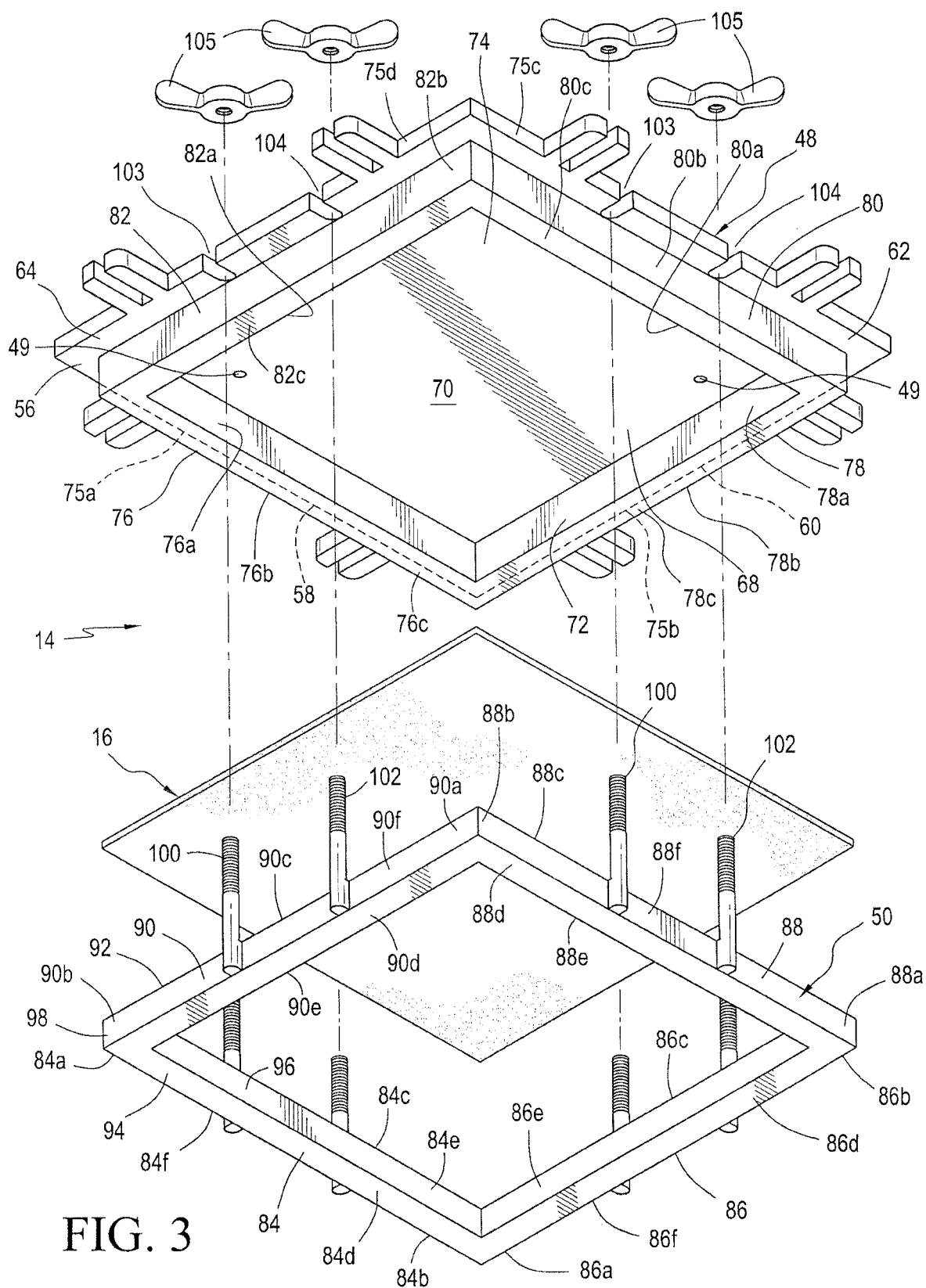
FIG. 3 is an exploded view of a liner support manifold.
Figure 4:
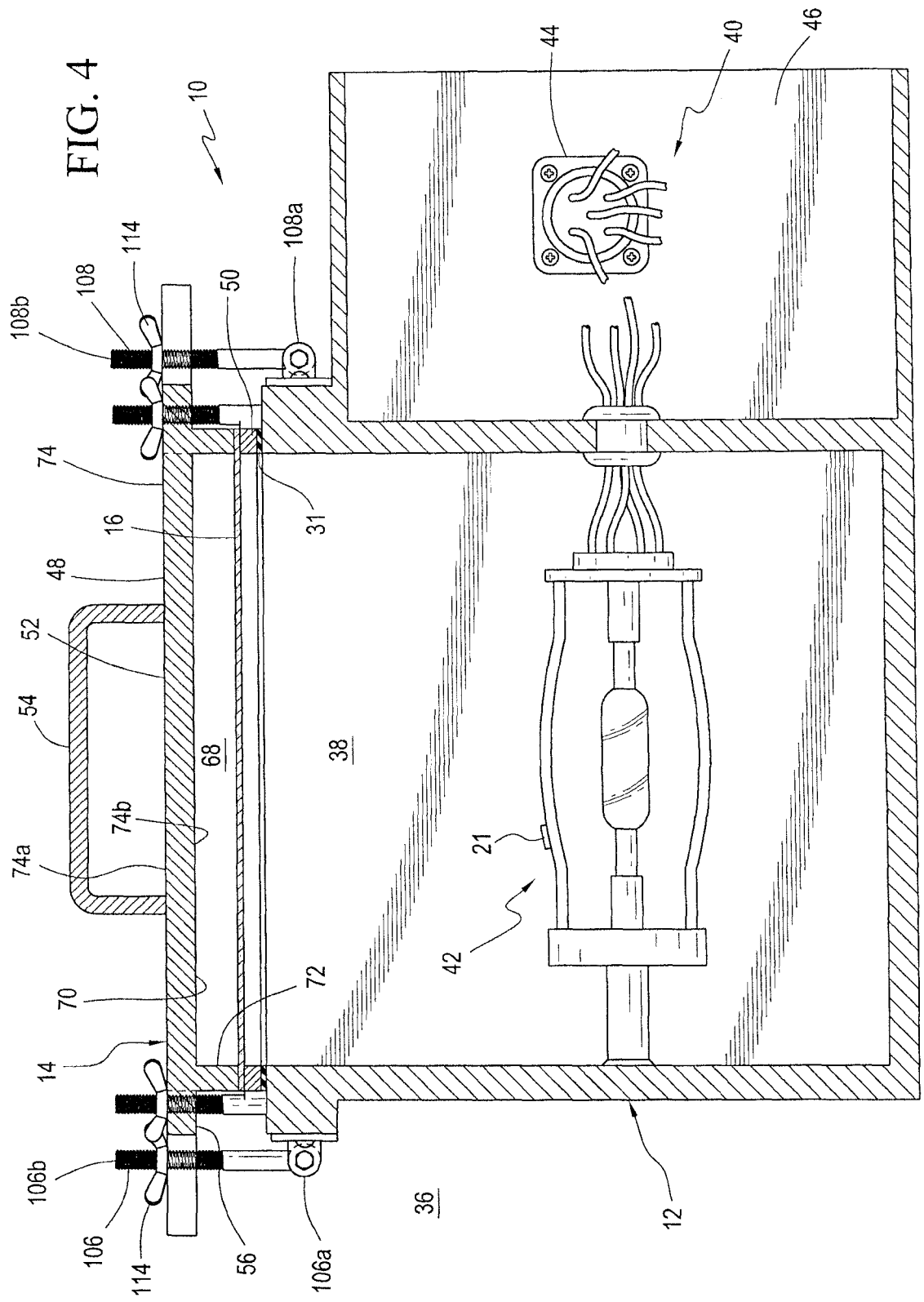
FIG. 4 is a cross sectional view along the line 4-4 in FIG. 1.
Figure 5:
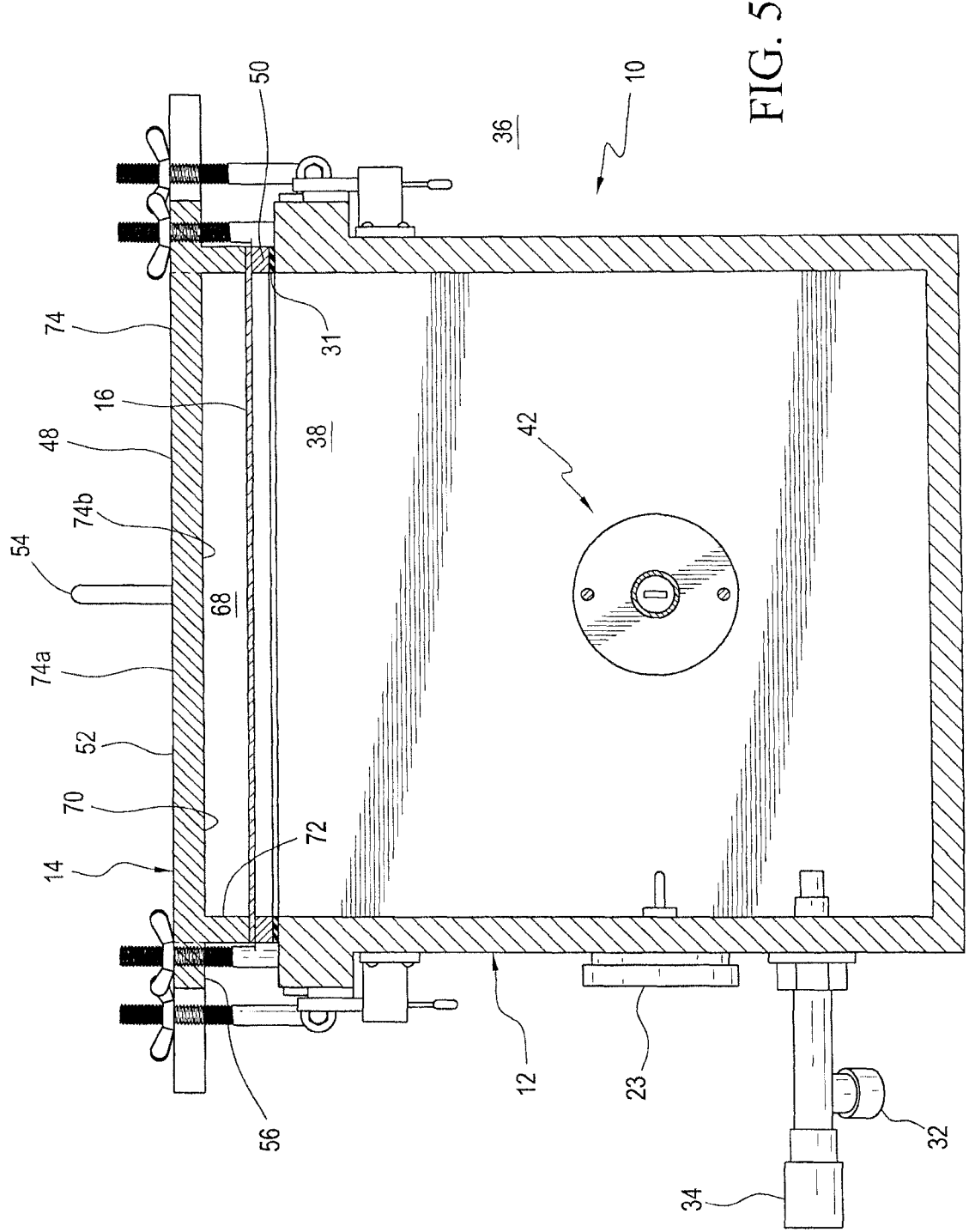
FIG. 5 is a cross sectional view along the line 5-5 in FIG. 1.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 7, a testing apparatus 10 is disclosed for onsite creation of cured sample liners necessary for confirming proper rehabilitation of pipelines. As discussed above, it is well appreciated that regulations require testing of pipeline liners to ensure the actual liner being cured within the pipeline (the in-ground liner) is fully and properly cured. Such cured liners are commonly resin impregnated fiberglass and require the application of ultraviolet (UV) light to ensure full and proper curing in place within the pipeline. The present testing apparatus 10 provides for testing of the in-ground liners without the necessity for removal of actual pieces of the in-ground liner from the pipeline so as to ensure the installed product meets all of the curing parameters unique to the liner to ensure the installed in-ground liner delivers the desired engineering properties. With this in mind, and as will be appreciated based upon the following disclosure, the present invention simulates the curing process by applying UV light and pressure to sample liner pieces in a manner that simulates the actual curing process. In particular, a sample liner will be processed (cured) in the field using the present testing apparatus 10 that utilizes the same UV light(s) used in the processing of the in-ground liner. As will be appreciated based upon the following disclosure, by recreating the stretch, or expansion, of the in-ground liner, the light intensity experienced in the curing (i.e. UV light distance from liner surface), internal pressure, and level of heating generated by the lamp(s) and the exothermic reaction of the resin, the present invention allows for the creation of a sample liner providing an accurate representation of the in-ground curing process that allows for making reliable measurements. With this in mind, and in contrast to actually cutting out a piece of the in-ground liner installed within a pipeline, the present testing apparatus 10 subjects a piece of sample liner 16 to the same environmental and UV light characteristics to which the installed in-ground liner is subjected.

The testing apparatus 10 includes a testing box 12 and a liner support manifold 14 that is ultimately secured to the testing box 12 for exposing the sample liner 16 to pressure and UV light in a highly controlled manner allowing for replication of the actual in-line curing processing. As will be explained below in greater detail, the testing box 12 is provided with inputs and outputs, as well as sensors and ultraviolet light sources, necessary to cure a sample liner 16 held by the liner support manifold 14. It will be appreciated that heat is a by-product of the curing process and as such is monitored in accordance with the present invention. However, the monitored heat is merely an indicator of the overall process and is not ultimately critical to the final curing of the sample liner.

The testing box 12 includes a base 20 having a plurality of upstanding side walls 22, 24, 26, 28. In accordance with a preferred embodiment, the base 20 is square shaped and includes a first upstanding side wall 22, a second upstanding side wall 24, a third upstanding side wall 26, and a fourth upstanding side wall 28 respectively extending from edges 20*a-d* of the square (or rectangular) shaped base 20. It is appreciated that although the present invention is disclosed herein with a square shape, the testing box may take various shapes depending upon the specifics of the liner being tested in accordance with the present invention. For example, where certain weave patterns of the liner are implemented it might be desirable to provide an elongated rectangular test box so as to optimize the sample produced as a result of the testing process. The testing box itself is primarily constructed from aluminum, although it is appreciated the testing box may be constructed from various metals depending upon cost, weight, and manufacturing considerations.

Each of the first, second, third, and fourth side walls 22, 24, 26, 28 includes a lower end 22*a*, 24*a*, 26*a*, 28*a* secured to an edge 20*a-d* of the square shaped base 20. The first, second, third, and fourth side walls 22, 24, 26, 28 are attached to each other along their respective adjacent upwardly extending edges. Finally, each of the first, second, third, and fourth side walls 22, 24, 26, 28 includes an upper edge 22*b*, 24*b*, 26*b*, 28*b*, wherein the upper edges 22*b*, 24*b*, 26*b*, 28*b* of the first, second, third and fourth side walls 22, 24, 26, 28 define an open upper end 30 of the testing box 12.

The testing box 12 also includes a pressure input 32 for attachment to a source of pressure, for example, coming from a curing truck as will be discussed below in greater detail, and a pressure output (or sensor coupling port) 34 for monitoring the pressure when the testing process is taking place. In accordance with a preferred embodiment, the pressure input 32 is integrated with the sensor coupling port 34 into a single valve assembly secured to the first side wall 22 and fluidly communicating between the exterior 36 and interior 38 of the testing box 12. A temperature gauge 23 is coupled to the first side wall 22 for ready observation of the temperature within the testing box 12. Although not shown, a pressure relief valve is integrated into the pressure supply line that would be secured to the pressure input 32 for supplying pressure in accordance with the present invention.

The testing box 12 includes an electrical power control assembly 40 and an ultraviolet light assembly 42. The ultraviolet light assembly 42 is positioned within the center of the cavity defined by the walls 22, 24, 26, 28 of the testing box 12. In accordance with the embodiment disclosed with reference to FIGS. 1 to 7, the ultraviolet light assembly 42 is fixedly mounted to side wall 20, 28 of the testing boxing 12. However, and in accordance with an alternate embodiment as shown with reference to FIGS. 8 to 11, the ultraviolet light assembly 242 may be mounted within the testing box 212 in a manner allowing for selective movement of the ultraviolet light assembly 242 toward or away from the sample liner 16 so as to replicate the different distances a curing light might be positioned from a liner within a pipeline based upon different pipeline diameters into which a liner is being installed. Given the ability to adjust the height of the ultraviolet light assembly 242 it is noted that the testing box 212 has a taller profile. This allows for variety in the distance the ultraviolet light assembly 242 will be positioned from the sample liner 16.

As such, the testing box 212 is provided with vertically oriented first and second support posts 244, 246 upon which the ultraviolet light assembly 242 is mounted for selective movement relative thereto. Each of the first and second support posts 244, 246 includes a first end 244a, 246a fixedly secured to the base 220 of the testing box 212 and a second end 244b, 246b extending upwardly within the testing box 212. Each of the first and second support posts 244, 246 also include a plurality of coupling holes 248 formed in an equidistant manner along the length of the support post 244, 246. The coupling holes 248 allow for the selective attachment of the ultraviolet light assembly 242 thereto through the use of coupling pins 250 that pass through both an elevated support beam 252 supporting the ultraviolet light assembly 242 and the coupling holes 248 of the support posts 244, 246.

The elevated support beam 252 is an elongated structure to which the ultraviolet light assembly 242 is secured. The elevated support beam 252 includes a central support bar 253 having a first end 254 with a C-shaped coupling arm 256 shaped and dimensioned to fit about the first support post 244 and a second end 258 with a C-shaped coupling arm 260 shaped and dimensioned to fit about the second support post 246. Each of the C-shaped coupling arms 256, 260 is provided with an aperture 262, 264 adapted for alignment with the coupling holes 248 of the first and second support posts 244, 246, respectively. As such, and when the elevated support beam 252 is mounted upon the first and second support posts 244, 246 with the C-shaped coupling arms 256, 260 wrapped thereabout, the elevated support beam 252 and ultraviolet light assembly 242 may be moved up and down relative to the first and second support posts 244, 246, and then locked in position by passing the coupling pins 250 through the aligned coupling holes 248 and apertures 262, 264 of the C-shaped coupling arms 256, 260. Movement of the ultraviolet light assembly 242 is further facilitated by the provision of a handle 266 on the central support bar 253 of the elevated support beam 252 that may be gripped by a user as he or she moves the ultraviolet light assembly 242 up and down as needed. In this way, the position of the ultraviolet light assembly 242 relative to the sample liner 16 may be adjusted to replicate the different distances a curing light might be positioned from a liner based upon different diameters of pipelines into which a liner is being installed. Other than the support assembly for the ultraviolet light assembly 242, the components of the embodiment disclosed with reference to FIGS. 8 to 11 are the same as those of the embodiment disclosed with reference to FIGS. 1 to 7 as described herein (and similar reference numerals are accordingly used).

The electrical power control assembly 40 includes a coupling member 44 for attachment to a source of power, for example, coming from a curing truck as will be discussed below in greater detail. The electrical power control assembly 40 is protected from the environment by a shroud 46 formed along the second side wall 24 of the testing box 12.

The liner support manifold 14 is shaped and dimensioned for supporting a sample liner 16 and for attachment to the open upper end 30 of the testing box 12 for exposing the sample liner 16 to pressure and ultraviolet light in accordance with the present invention. The liner support manifold 14 includes a cover member 48 and a frame coupling member 50 between which the sample liner 16 is mounted.

The cover member 48 includes a top 52 with a handle 54 secured thereto and a bottom 56 upon which the sample liner 16 is mounted in a manner described below in greater detail. Extending between the top 52 and the bottom 56 are a plurality of side walls (in particular, and as defined below in greater detail, first, second, third, and fourth side walls 75a-d of top plate 74) defining the outer periphery of the cover member 48. In accordance with a preferred embodiment the outer periphery is shaped and dimensioned so as to fully cover the opening 66 defined by the upper edges 22b, 24b, 26b, 28b of the first, second, third, and fourth side walls 22, 24, 26, 28. With this in mind, the cover member 48 is preferably square or rectangular shaped when viewed from above and looking downward upon the top 52 thereof. The bottom 56 of the cover member 48 includes a recess 68 into which the sample liner 16 will form as it is cured under ultraviolet light and pressure in accordance with the present invention. Because the liner will move upwardly into the recess 68 during the testing process, the cover member 48 is provide with at least one relief hole (in accordance with a disclosed embodiment two such holes are provided) 49 so as to allow for the evacuation of any pressure between the bottom 56 of the cover member 48 and the sample liner 16 as the sample liner 16 moves toward the bottom 56 of the cover member 48 during the testing process.

Figure 6:
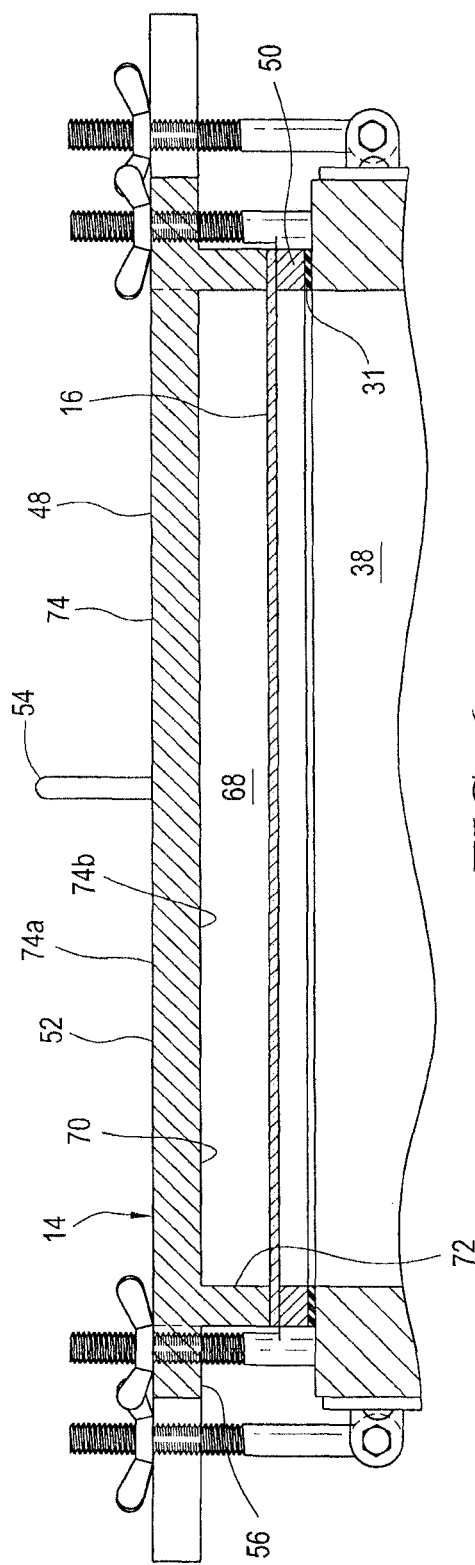
FIGS. 6 and 7 are respectively detailed cross sectional views showing the sample liner before and after processing in accordance with the present invention.
Figure 7:
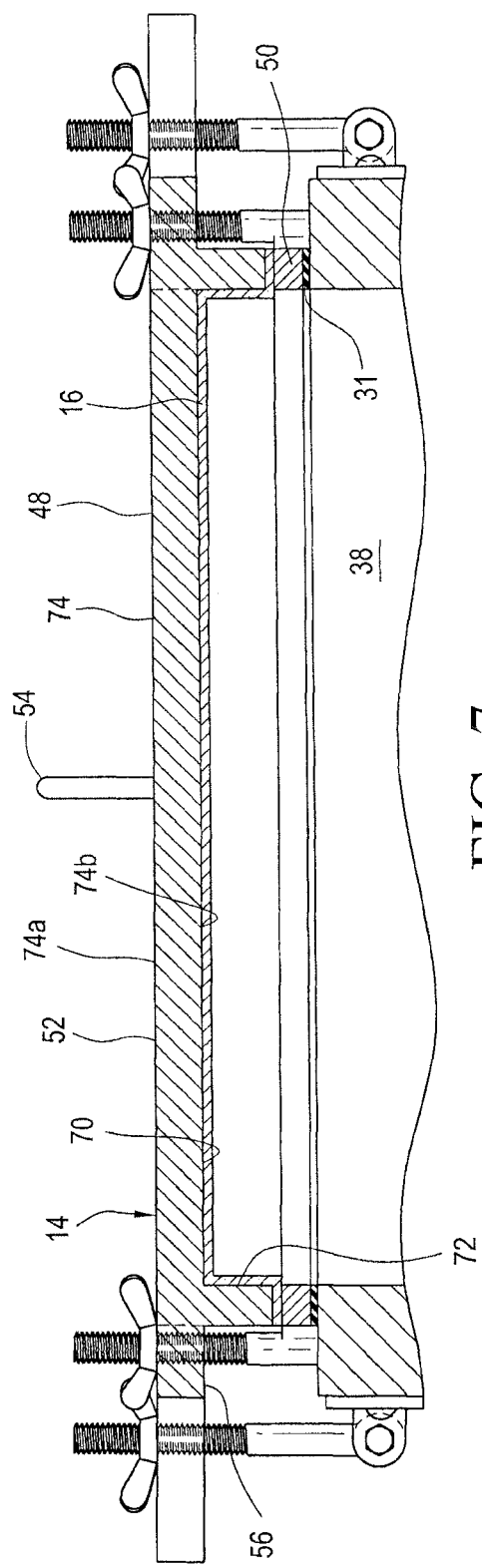
Figure 8:
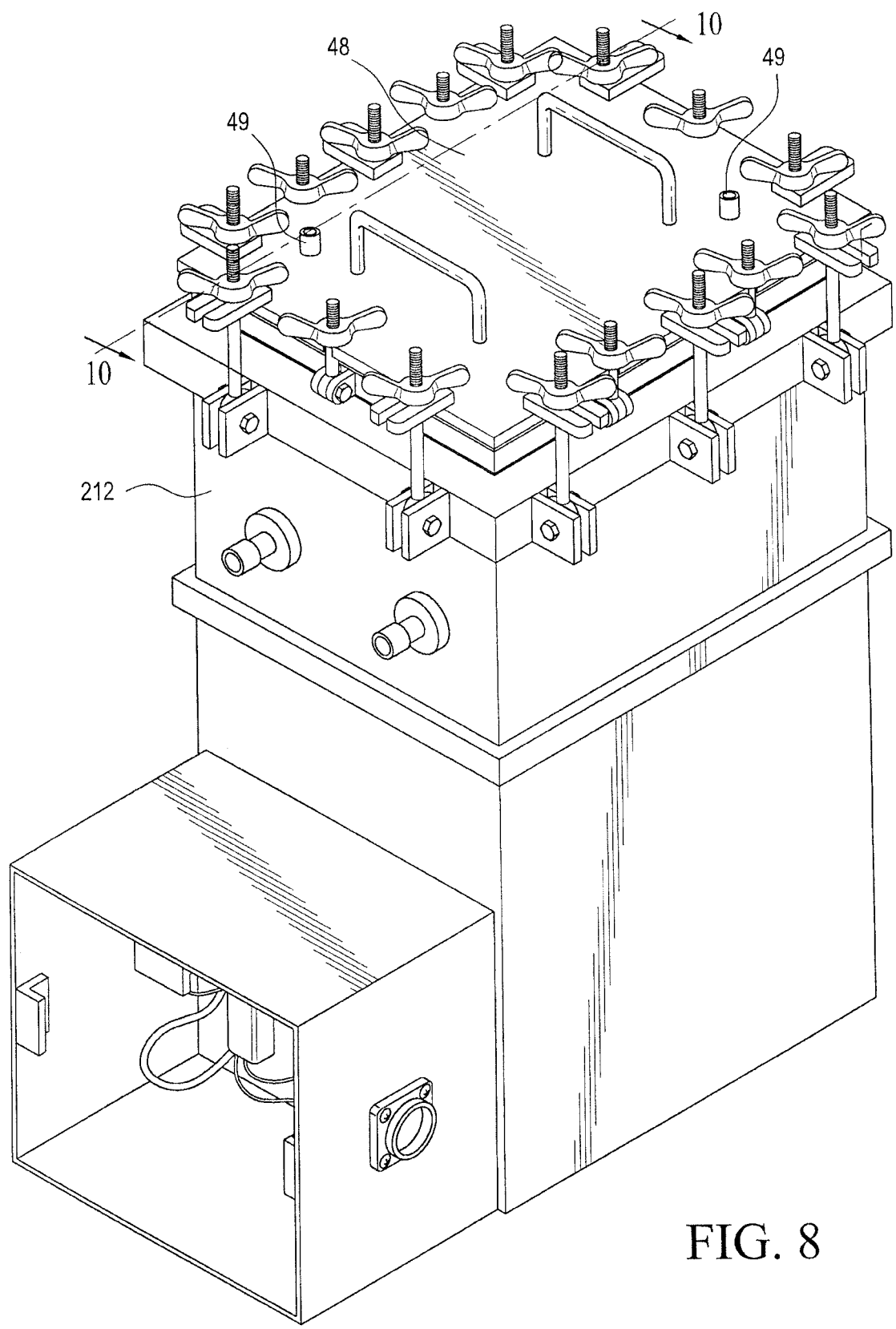
FIG. 8 is a perspective view of an alternate embodiment of the testing apparatus in accordance with the present invention.
Figure 9:
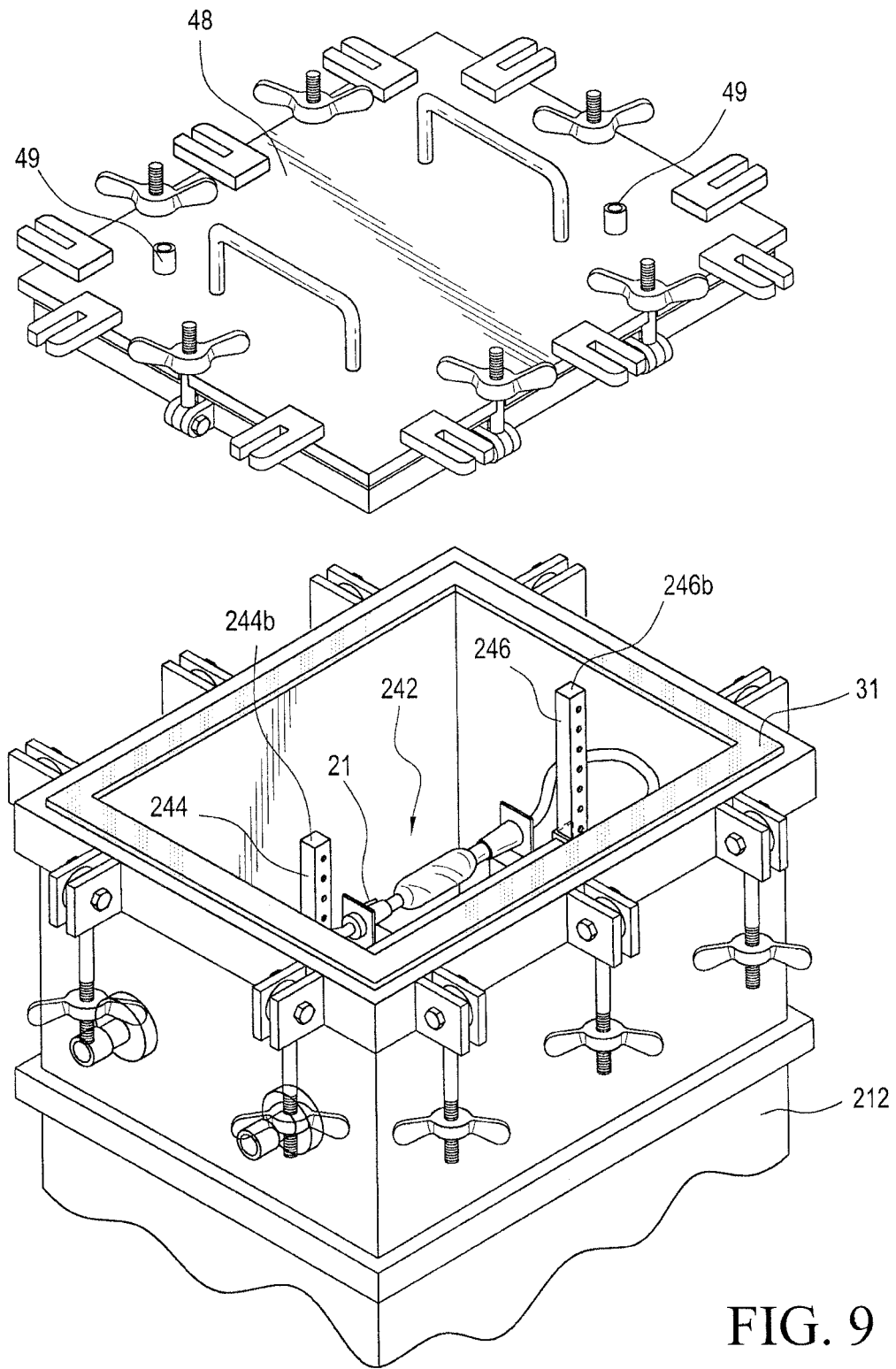
FIG. 9 is an exploded view of the testing apparatus shown in FIG. 8.
Figure 10:
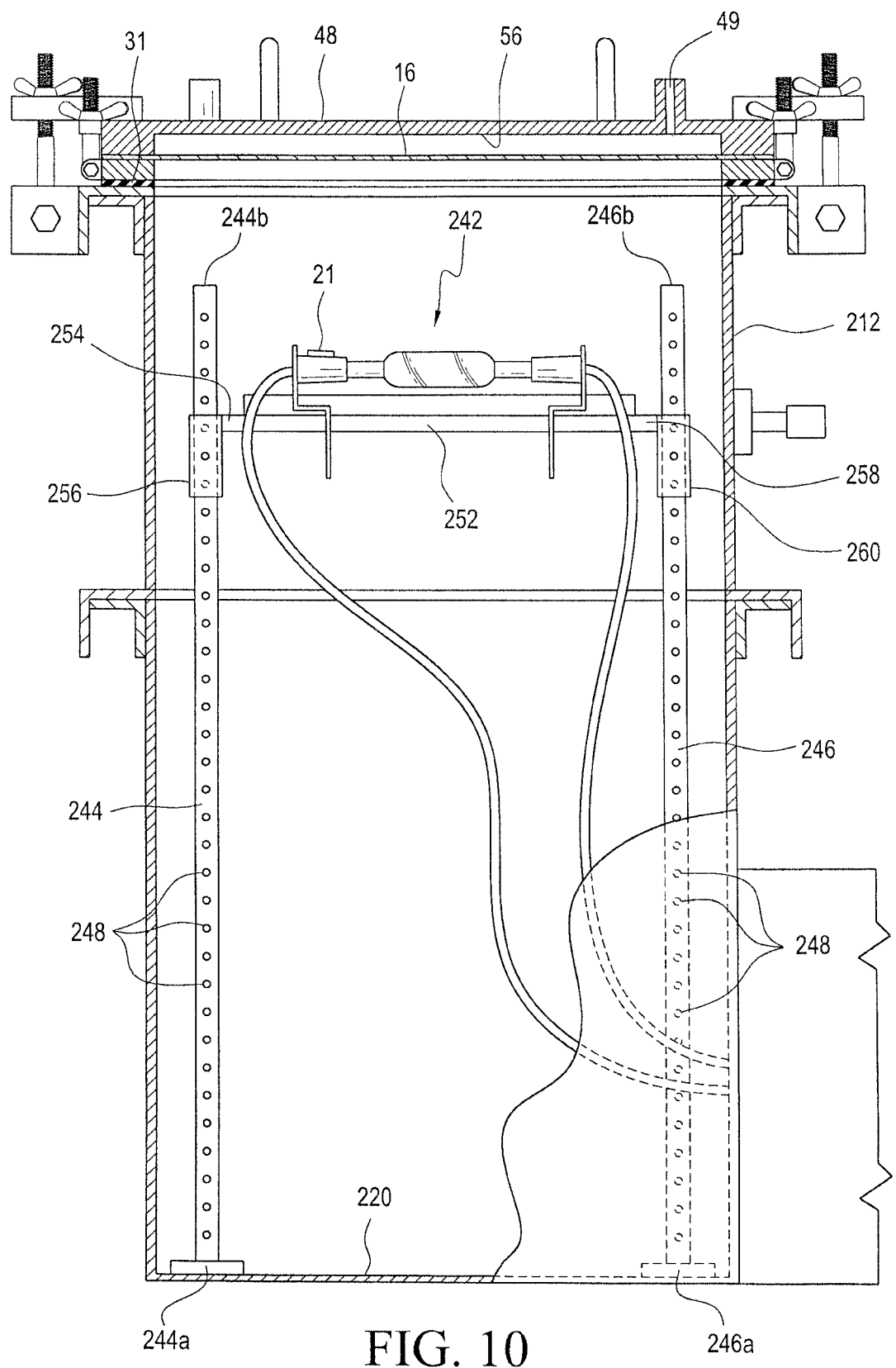
FIG. 10 is a cross sectional view along the line 10-10 in FIG. 8.
Figure 11:
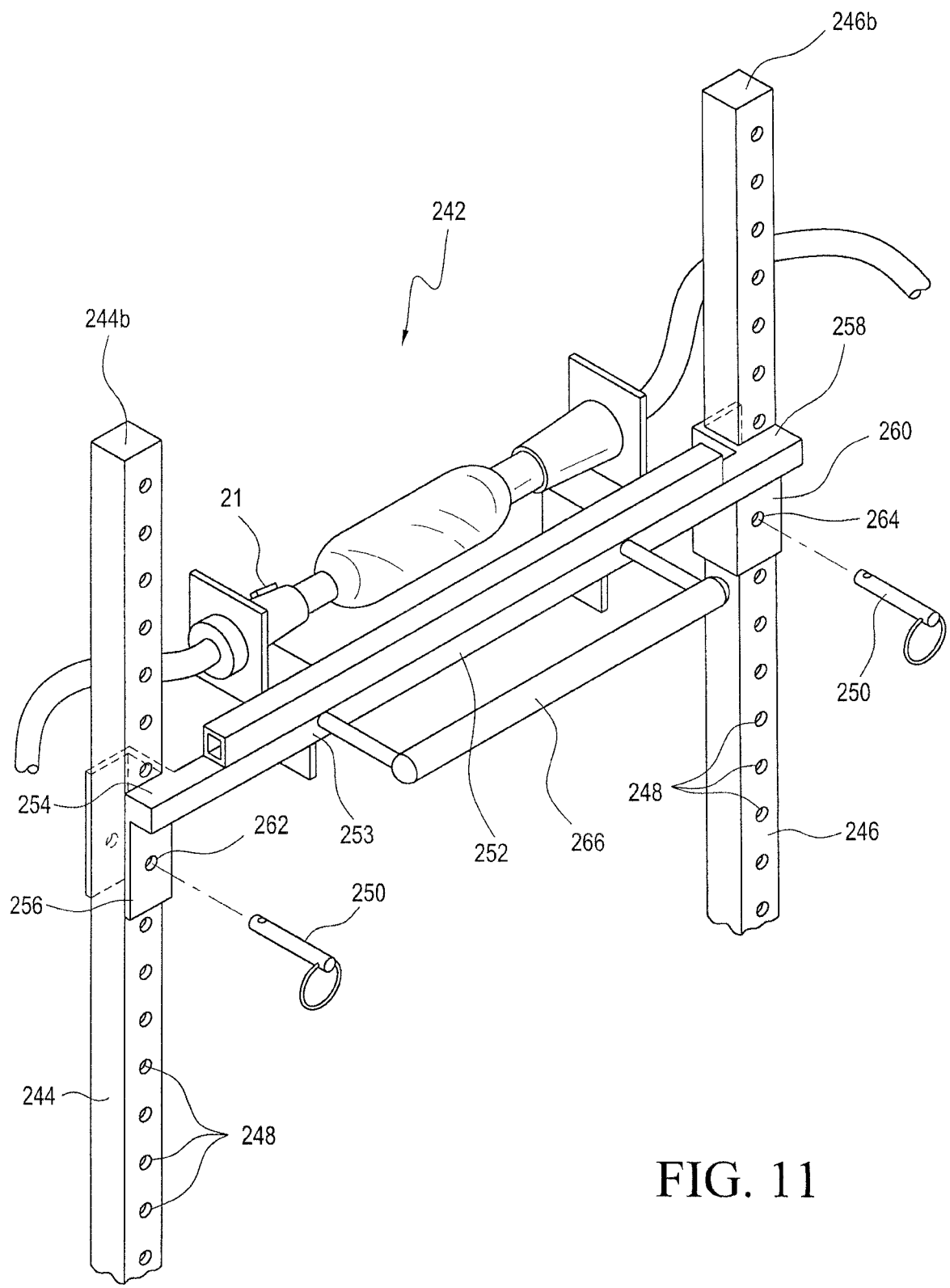
FIG. 11 is a perspective view of the support assembly for the ultraviolet light assembly in accordance with the embodiment disclosed with reference to FIGS. 8-10.

The recess 68 includes a generally planar portion 70 along the central portion thereof and a boundary 72 positioned about the periphery thereof so as to define the recess 68 into which the sample liner 16 will be formed during the curing process. As will be appreciated, when a liner is cured within a pipeline it is subjected to expansive pressure that causes the liner to expand when it is forced into the wall of the pipeline. Similarly, the present testing box 12 allows for expansion of the sample liner 16 during the curing process in a manner that replicates actual curing within the pipeline (see FIGS. 6 and 7 showing the sample liner 16 before and after processing in accordance with the present invention). With this in mind, liners commonly range in thickness from 2.8 mm to 24 mm and will therefore exhibit different expansion characteristics. Accordingly, the depth of the recess may be varied to produce desired expansion characteristics as the liners are cured in accordance with the present invention.

More particularly, the cover member 48, in accordance with a preferred embodiment, is composed of a cover plate 74 that defines the top 52 of the cover member 48 along a first side 74a of the cover plate 74 and the planar portion 70 of the bottom 56 along a second side 74b of the cover plate 74 (opposite the first side 74a). The recess 68 is defined by downwardly extending first, second, third, and fourth walls 76, 78, 80, 82 which are connected at their respective ends to define, in conjunction with the second side 74b of the cover plate 74, the concave recess 68 of the cover member 48. Each of the first, second, third, and fourth walls 76, 78, 80, 82 includes an inner surface 76a, 78a, 80a, 82a, an outer surface 76b, 78b, 80b, 82b and a bottom surface 76c, 78c, 80c, 82c. The inner surface 76a, 78a, 80a, 82a of each of the first, second, third, and fourth walls 76, 78, 80, 82 is shaped to define the outer boundary 72 of the recess 68 of the cover member 48. The outer surface 76b, 78b, 80b, 82b of each of the first, second, third, and fourth walls 76, 78, 80, 82 is inwardly spaced from the outer side walls 75a-d of the cover plate 74 to allow for space in coupling the frame coupling member 50 to the cover member 48 as will be better appreciated based upon the following disclosure. The bottom surface 76c, 78c, 80c, 82c of each of the first, second, third, and fourth walls 76, 78, 80, 82 is planar and is shaped and dimensioned for alignment with the frame coupling member 50 so that a sample liner 16 may be secured therebetween.

Considering the bottom surface 76c, 78c, 80c, 82c of each of the first, second, third, and fourth walls 76, 78, 80, 82, they provide a support for the sample liner 16 as it is forced within the recess 68. It is important when securing the sample liner 16 to the bottom surface 76c, 78c, 80c, 82c of each of the first, second, third, and fourth walls 76, 78, 80, 82, and between the cover member 48 and the frame coupling member 50, that the sample liner 16 not sag into the recess 68. Rather, the liner 16 should be positioned and mounted so that it sits upon the bottom surface 76c, 78c, 80c, 82c of each of the first, second, third, and fourth walls 76, 78, 80, 82 in a relatively flat configuration. As such, and when pressure is applied to cure the liner in accordance with the present invention, the sample liner 16 will be stretched to conform to the surface defined by the recess 68 in a manner replicating the stretching that occurs during the curing of a liner in a pipeline. With this in mind, and considering the different stretching characteristics of different liners it may be desirable to provide a shim member for positioning above the bottom surface 76c, 78c, 80c, 82c of each of the first, second, third, and fourth walls 76, 78, 80, 82 so as to space the sample liner 16 further from the flat surface 70 of the cavity 68 thus resulting in greater stretching of the sample liner 16 when pressure is applied.

The frame coupling member 50 includes first, second, third, and fourth elongated members 84, 86, 88, 90 coupled together at their respective ends. Each of the first, second, third, and fourth elongated members 84, 86, 88, 90 includes a first end wall 84a, 86a, 88a, 90a, a second end wall 84b, 86b, 88b, 90b, a top wall 84c, 86c, 88c, 90c, a bottom wall 84d, 86d, 88d, 90d, an interior wall 84e, 86e, 88e, 90e, and an exterior wall 84f, 86f, 88f, 90f. The top wall 84c, 86c, 88c, 90c of each of the first, second, third, and fourth elongated members 84, 86, 88, 90 together define the upper surface 92 of the frame coupling member 50. The bottom wall 84d, 86d, 88d, 90d of each of the first, second, third, and fourth elongated members 84, 86, 88, 90 together define the lower surface 94 of the frame coupling member 50. The interior wall 84e, 86e, 88e, 90e of each of the first, second, third, and fourth elongated members 84, 86, 88, 90 together define the interior periphery 96 of the frame coupling member 50. The exterior wall 84f, 86f, 88f, 90f of each of the first, second, third, and fourth elongated members 84, 86, 88, 90 together define the exterior surface 98 of the frame coupling member 50.

Attached to each of the exterior walls 84f, 86f, 88f, 90f of the first, second, third, and fourth walls 84, 86, 88, 90 of the frame coupling member 50 are upwardly extending (that is, extending from the lower surface 94 of the frame coupling member 50 to a position above the upper surface 92 of the frame coupling member 50) equally spaced first and second securing bolts 100, 102. The first and second securing bolts 100, 102 are shaped and dimensioned for positioning within recesses 103, 104 formed in the side walls 75a-d of the cover plate 74. With the frame coupling member 50 positioned beneath the cover member 48 and in alignment with the bottom surfaces 76c, 78c, 80c, 82c of the first, second, third, and fourth walls 76, 78, 80, 82, wing nuts 105 may be secured to the securing bolts 100, 102 to draw the frame coupling member 50 and the cover member 48 together until sufficient pressure is created to hold the frame coupling member 50 and the cover member 48 together with the sample liner 16 secured therebetween.

As will be explained below in further detail, the testing box 12 and the liner support manifold 14 are adapted for selective attachment such that the liner support manifold 14 is secured to the open upper end 30 of the testing box 12. With this in mind, the exterior of the first, second, third, and fourth side walls 22, 24, 26, 28 are provide with equally spaced first and second securing swing bolts 106, 108. Each of the securing swing bolts 106, 108 includes a first end 106a, 108a pivotally secured to the exterior of each of the first, second, third, and fourth side walls 22, 24, 26, 28 as well as a second end 106b, 108b shaped and dimensioned for interaction with the liner support manifold 14 so as to securely mount the liner support manifold 14 upon the testing box 12.

Each of the first, second, third, and fourth side walls 75a-d of the top plate 74 of the cover member 48 of the liner support manifold 14 are provided with equally spaced outwardly extending first and second coupling members 110, 112 including bolt recesses 110a, 112a. In particular, the first and second coupling members 110, 112 extend outwardly from the side walls 75a-d of the cover plate 74 such that the coupling members 110, 112 lie in a plane the same as, or substantially parallel to, the plane in which the cover plate 74 of the cover member 48 lies. Securing is achieved by positioning the second end 106b, 108b of the securing swing bolt 106, 108 within the bolt recess 110a, 112a of the coupling member 110, 112 and applying a wing nut 114 to the second end 106b, 108b of the swing bolt 106, 108 to draw the liner support manifold 14 toward the testing box 12 until sufficient pressure is created to hold the liner support manifold 14 and the testing box 12 together.

The testing apparatus 10 is used in the following manner. First, a sample liner 16 is installed within the liner support manifold 14. This is accomplished by placing the frame coupling member 50 upon a support surface and positioning a piece of plywood having the same thickness as the frame coupling member 50 within the interior periphery 96 of the frame coupling member 50. The sample liner 16 is then placed over the frame coupling member 50 such that it sits upon the top walls 84c, 86c, 88c, 90c of the first, second, third, and fourth elongated members 84, 86, 88, 90. The sample liner 16 is also supported by the plywood such that it does not sag during this process.

With the cover member 48 having the top 52 thereof facing upwardly and the bottom 56, in particular, the concave recess 68, facing downwardly, the cover member 48 is placed on top of the sample liner 16. The cover member 48 is positioned such that the bottom surfaces 76c, 78c, 80c, 82c of the first, second, third, and fourth walls 76, 78, 80, 82 sit upon the sample liner 16 with the concave recess 68 facing the sample liner 16. In this position the securing bolts 100, 102 of the frame coupling member 50 are positioned within the recesses 103, 104 formed along the side walls 75a-d of the cover plate 74. The wing nuts 105 are then screwed down onto the securing bolts 103, 104 to securely sandwich the sample liner 16 between the cover member 48 and the frame coupling member 50 such that all of these components are securely held together.

The liner support manifold 14, with the sample liner 16 supported thereby, may then be secured to the testing box 12. With the sample liner 16 facing downwardly, the liner support manifold 14 is placed upon the open upper end 30 of the testing box 12 such that the frame coupling member 50 is aligned with the upper ends 22b, 24b, 26b, 28b of the side walls 22, 24, 26, 28 of the testing box 12. In accordance with a preferred embodiment, a rubber sealing member 31 is positioned between the liner support manifold 14 and the open upper end 30 of the testing box 12 such that the sealing member 31 is positioned between the frame coupling member 50 and the upper ends 22b, 24b, 26b, 28b of the side walls 22, 24, 26, 28 of the testing box 12. The liner support manifold 14 is then secured to the testing box 12. In particular, the first and second securing swing bolts 106, 108 along each of the first, second, third, and fourth side walls 22, 24, 26, 28 are pivoted upwardly such that the second end 106b, 108b of the securing swing bolt 106, 108 is within the recess 110a, 112a of the respective coupling members 110, 112 and a wing nut 114 is applied to the second end 106b, 108b of the securing swing bolt 106, 108 to draw the liner support manifold 14 toward the testing box 12 until sufficient pressure is created to hold the liner support manifold 14 and the testing box 12 together.

Thereafter, the testing apparatus 10 is placed under pressure to match the recommended pressure from the manufacturer. The cure truck 310, which controls curing of the real liner in the ground, is attached to the testing box 12 (that is, the pressure line 311 and pressure source 312 of the cure truck 310 are coupled to the pressure input 32 of the testing box 12, the pressure sensor(s) 314 of the cure truck 310 is coupled to the sensor coupling port 34 via a pressure line 317, and the electrical power source 316 of the cure truck 310 is coupled to electrical power control assembly 40 via a power & control line 318 connected to the coupling member 44 for powering the ultraviolet light assembly 42 and obtaining readings from IR sensor 21 and temperature gauge 23, as well as other sensors that may be used in conjunction with the testing box 12) and will apply the exact same operational parameters as it does in conjunction with the liner within the pipeline, for example, the same pressure, wattage and the like will be applied in accordance with testing.

By way of example, the sample liner 16 is first subjected to optimal pressures known to those skilled in the art. Once the desired pressure is established within the testing apparatus 10, the ultraviolet light assembly 42 is energized to achieve optimal cure as known to those skilled in the art. During this process all applied and measured parameters are stored within a memory device 320 on the cure truck 310 for later analysis. In accordance with a preferred embodiment, the measured parameters may include, but are not limited to the temperature of the sample liner 16 as measured by an IR sensor 21 housed within the testing box 12 (that reads the actual temperature increase of the sample liner 16 due to the sample liner's exothermic reaction that is indicative of the curing process taking place), the temperature within the testing apparatus 10 as measured by the temperature gauge 23, the pressure within the testing apparatus 10 as measured by the pressure sensor(s) 314 of the cure truck 310 coupled to the sensor coupling port 34 via a pressure line 317, and applied wattage as measured via the electrical power control assembly 40. Once the application pressure and ultraviolet light is completed, the sample liner 16 may be removed from the testing apparatus 10 and analyzed, in conjunction with the stored data, to determine whether proper curing has taken place.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A testing apparatus for onsite creation of cured sample liners necessary for confirming proper rehabilitation of pipelines, comprising:
a testing box for curing of a sample liner; and
a liner support manifold shaped and dimensioned for supporting the sample liner and for attachment to the testing box for exposing the sample liner to conditions for curing of the sample liner, the liner support manifold including a cover member and a frame coupling member between which the sample liner is mounted;
the frame coupling member includes a plurality of elongated members coupled together at respective ends, wherein top walls of the plurality of elongated members define an upper surface of the frame coupling member and bottom walls of the plurality of elongated members define a lower surface of the frame coupling member, both the upper surface and the lower surface define respective openings such that the upper surface of the frame coupling member is shaped and dimensioned for alignment with the cover member such that the sample liner may be selectively positioned therebetween, and the lower surface is shaped and dimensioned for alignment with an open upper end of the testing box;
wherein, and with the sample liner secured to the liner support manifold in a position between the upper surface of the frame coupling member and the cover member and the liner support manifold secured to the testing box such that the frame coupling member is between the cover member and the testing box, the sample liner is exposed to conditions for curing of the sample liner in a highly controlled manner allowing for replication of actual in-line curing processing.

2. The testing apparatus according to claim 1, wherein the testing box includes a pressure input for attachment to a source of pressure and a pressure output for monitoring the pressure when the testing process is taking place.

3. The testing apparatus according to claim 1, wherein testing box includes a temperature gauge for ready observation of the temperature within the testing box.

4. The testing apparatus according to claim 1, wherein a rubber sealing member is positioned between the liner support manifold and the testing box.

* * * * *